(12) United States Patent
Dalko et al.

(10) Patent No.: US 7,326,717 B2
(45) Date of Patent: Feb. 5, 2008

(54) PYRIMIDINE N-OXIDE COMPOUNDS FOR STIMULATING THE GROWTH OF KERATIN FIBERS AND/OR REDUCING LOSS THEREOF

(75) Inventors: Maria Dalko, Gif s/Yvette (FR); Yann Mahe, Morsang sur Orge (FR); Marie-Madeleine Cals-Grierson, Meudon (FR)

(73) Assignee: L'Oreal, Paris (FR)

( * ) Notice: Subject to any disclaimer, the term of this patent is extended or adjusted under 35 U.S.C. 154(b) by 456 days.

(21) Appl. No.: 10/839,176

(22) Filed: May 6, 2004

(65) Prior Publication Data

US 2005/0130991 A1    Jun. 16, 2005

Related U.S. Application Data

(60) Provisional application No. 60/507,495, filed on Oct. 2, 2003.

(30) Foreign Application Priority Data

May 6, 1930    (FR)    ................... 03 50145

(51) Int. Cl.
C07D 238/48    (2006.01)
C07D 239/50    (2006.01)
A61K 31/506    (2006.01)
(52) U.S. Cl. ..................... 514/275; 544/323
(58) Field of Classification Search ............... 544/323; 514/275
See application file for complete search history.

(56) References Cited

U.S. PATENT DOCUMENTS

| | | | |
|---|---|---|---|
| 3,382,247 A | 5/1968 | Anthony et al. | |
| 4,910,226 A | 3/1990 | Holt et al. | |
| 4,973,474 A | 11/1990 | Hocquaux et al. | |
| 5,132,106 A | 7/1992 | Tuloup et al. | |
| 5,328,914 A | 7/1994 | Hocquaux et al. | |
| 5,411,981 A | 5/1995 | Gaillard-Kelly et al. | |
| 5,438,058 A | 8/1995 | Dufetel et al. | |
| 5,466,694 A | 11/1995 | Terranova et al. | |
| 5,468,888 A | 11/1995 | Bouboutou et al. | |
| 5,480,913 A | 1/1996 | Liao et al. | |
| 5,516,779 A | 5/1996 | Von Langen et al. | |
| 5,529,769 A | 6/1996 | Cho et al. | |
| 5,565,467 A | 10/1996 | Batchelor et al. | |
| 5,631,282 A | 5/1997 | Goetz | |
| 5,650,145 A | 7/1997 | Saint-Leger | |
| 5,756,092 A | 5/1998 | Michelet et al. | |
| 5,760,043 A | 6/1998 | Dufetel et al. | |
| 5,772,990 A | 6/1998 | Hocquaux et al. | |
| 5,846,552 A | 12/1998 | Mahe et al. | |
| 6,465,421 B1 | 10/2002 | Duranton et al. | |
| 6,468,972 B1 | 10/2002 | Pruche et al. | |
| 2002/0044953 A1 | 4/2002 | Michelet et al. | |
| 2002/0045659 A1 | 4/2002 | Michelet et al. | |
| 2003/0083381 A1 | 5/2003 | Kumagai et al. | |

FOREIGN PATENT DOCUMENTS

| | | |
|---|---|---|
| BE | 1003002 A | 10/1991 |
| EP | 0 327 263 A1 | 8/1989 |
| EP | 0 408 442 A1 | 1/1991 |
| EP | 0 459 890 A1 | 12/1991 |
| EP | 0 522 964 A1 | 1/1993 |
| EP | 0 648 488 A1 | 4/1995 |
| EP | 0 680 745 A2 | 11/1995 |
| EP | 0 770 399 A2 | 5/1997 |
| EP | 0 854 700 B1 | 7/1998 |
| EP | 1 175 890 A1 | 1/2002 |

(Continued)

OTHER PUBLICATIONS

Pinnell et al., PubMed Abstract (Dermatologica, 175 Suppl. 2: 12-8) 1987.*
Sonis et al., The Pathobiology of Mucositis, Nat Rev Cancer 4(4):277-284, 2004.*

*Primary Examiner*—Deepak Rao
(74) *Attorney, Agent, or Firm*—Buchanan, Ingersoll & Rooney, PC

(57) ABSTRACT

Novel pyrimidine N-oxide compounds and salts thereof, well suited for stimulating the growth of keratin fibers (e.g., the hair or the eyelashes) and/or limiting the loss thereof and/or increasing their density, have the formula (A):

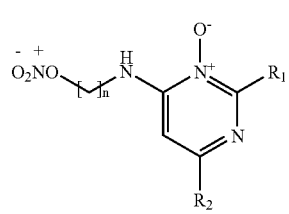

in which n is an integer ranging from 2 to 12; $R_1$ is a linear or branched, saturated or unsaturated alkyl radical, optionally substituted with a group —OR', —NR'R" or —COOR', $R_1$ having from 1 to 20 carbon atoms, or is NR'R"; $R_2$ is hydrogen, —$NR_3R_4$, —$OR_3$, or —$SR_3$, wherein $R_3$ and $R_4$, which may be identical or different, are each a linear or branched, saturated or unsaturated alkyl radical, optionally substituted with a group —OR', —NR'R" or —COOR', $R_2$ having from 1 to 20 carbon atoms, with the proviso that $R_3$ and $R_4$ may form part of a saturated or unsaturated ring member of 4 to 7 atoms, optionally containing at least one hetero atom; and R' and R", which may be identical or different, are each hydrogen or a saturated, linear or branched $C_1$-$C_3$ alkyl radical.

21 Claims, No Drawings

FOREIGN PATENT DOCUMENTS

| | | |
|---|---|---|
| EP | 1 175 891 A1 | 1/2002 |
| FR | 2 268 523 | 11/1975 |
| GB | 2 198 132 A | 6/1988 |
| GB | 2198132 * | 6/1988 |
| JP | 1-238543 A | 9/1989 |
| JP | 7-316023 A | 12/1995 |
| JP | 9-295921 A | 11/1997 |
| JP | 10-287532 A | 10/1998 |
| WO | 94/06434 A1 | 3/1994 |
| WO | 94/22468 A1 | 10/1994 |
| WO | 95/11003 A1 | 4/1995 |
| WO | 96/09048 A1 | 3/1996 |
| WO | 98/33497 A1 | 8/1998 |
| WO | 99/13717 | 3/1999 |
| WO | 01/72268 A1 | 10/2001 |
| WO | 01/74307 A2 | 10/2001 |
| WO | 01/74313 A2 | 10/2001 |
| WO | 01/74314 A2 | 10/2001 |
| WO | 01/74315 A2 | 10/2001 |

* cited by examiner

US 7,326,717 B2

PYRIMIDINE N-OXIDE COMPOUNDS FOR STIMULATING THE GROWTH OF KERATIN FIBERS AND/OR REDUCING LOSS THEREOF

CROSS-REFERENCE TO PRIORITY/PROVISIONAL APPLICATIONS

This application claims priority under 35 U.S.C. § 119 of FR-03/50145, filed May 6, 2003, and of provisional application Ser. No. 60/507,495, filed Oct. 2, 2003, both hereby expressly incorporated by reference and both assigned to the assignee hereof.

BACKGROUND OF THE INVENTION

1. Technical Field of the Invention

The present invention relates to cosmetic or pharmaceutical compositions containing an effective amount of a pyrimidine N-oxide compound, for inducing and/or stimulating the growth of human keratin fibers and in particular the hair and the eyelashes, and/or for reducing their loss.

This invention also relates to a cosmetic treatment process (regime or regimen) for stimulating the growth of human keratin fibers such as the hair and the eyelashes and/or for reducing their loss, and to the use of the subject pyrimidine N-oxide compounds as NO-donating active agents and/or as agents for inhibiting lysyl-hydroxylase, in particular for inducing and/or stimulating the growth of the hair or the eyelashes and/or for reducing their loss.

The present invention also relates to novel pyrimidine N-oxide compounds with NO-donating and/or lysyl-hydroxylase inhibiting activity.

2. Description of Background and/or Related and/or Prior Art

Hair growth and hair renewal are mainly determined by the activity of the hair follicles and of their matrix environment. Their activity is cyclical and comprises essentially three phases, namely, the anagenic phase, the catagenic phase and the telogenic phase.

The anagenic phase (active phase or growth phase), which lasts several years and during which the hair gets longer, is followed by a very short and transient catagenic phase which lasts a few weeks. During this phase, the hair undergoes a change, the follicle becomes atrophied and its dermal implantation appears higher and higher.

The terminal phase or telogenic phase, which lasts a few months, corresponds to a resting phase of the follicle and the hair ends up falling out. At the end of this rest period, a new follicle is regenerated in situ and another cycle begins.

The head of hair is thus under permanent renewal, and, out of the approximately 150,000 hairs that make up a head of hair, about 10% are at rest and will be replaced within a few months.

In adulthood, the vascular system of the skin is complete and no longer changes, except in the hair follicles, where it undergoes large changes with each hair cycle. Specifically, the hair follicles are a richly innervated and highly vascularized cutaneous structure. The phenomenon of development of capillary circulation in the hair follicles is known as angiogenesis. At the start of each anagenic phase, it is necessary to develop a high activation of angiogenesis in order to redevelop the perifollicular vascular capillary network. The involution of this capillary network and the disappearance of the blood vessels of the dermal papilla go hand in hand with the change of phase and the passage into the catagenic phase. At this stage, the blood capillaries collapse and disappear.

In parallel, in the alopecic areas, a perifollicular fibrosis becomes established, the follicles reduce in size cycle after cycle and the specific vascularization of the bulbs gradually diminishes.

The phenomenon of angiogenesis observed during the anagenic phase is dependant on many trophic factors, cytokines or other biologically active molecules provided by the blood circulation or produced locally, in particular by the fibroblasts of the dermal papilla or the keratinocytes of the hair bulb. Among these trophic factors, mention may be made of endothelial cell growth factor (also known as vascular endothelial growth factor (VEGF)). This factor is essential for angiogenesis and increases the vascular permeability. Studies have shown that the expression of this factor was increased during the anagenic phase of the hair cycle. Thus, this factor contributes towards maintaining a functional capillary vascularization around the hair follicle and especially at the base of the bulb and of the dermal papilla, and also towards supplying nutrients required for good growth of the hair.

The perifollicular capillary circulation thus plays a fundamental role in the process of hair growth by supplying the factors and nutrients required for the growth of this follicle.

The natural loss or falling-out of the hair may be estimated, on average, as being a few hundred hairs per day for a normal physiological state. This process of permanent physical renewal undergoes a natural change during aging; the hairs become finer and their cycles shorter.

Moreover, in certain dermatoses of the scalp with an inflammatory component, for instance psoriasis or seborrhoeic dermatitis, hair loss may be greatly accentuated and the follicle renewal cycle may be highly disrupted.

In addition, various causes may result in a substantial, temporary or permanent loss of hair. This may be loss and impairment of hair at the terminal stage of pregnancy (post-partum), during states of dietary malnutrition or imbalance, or during states of asthenia or of hormonal dysfunction, as may be the case during or at the terminal stage of the menopause. It may also be a case of loss or impairment of the hair related to seasonal phenomena.

It may also be a matter of alopecia, which is essentially due to a disturbance in hair renewal, resulting, in a first stage, in acceleration of the frequency of the cycles to the detriment of the quality of the hair, and then of their quantity. This then results in a gradual impoverishment of the head of hair and in gradual thinning of the hair together with isolation of the bulbs due to progressive thickening of the perifollicular collagen matrix and of the outer connective sheath. Revascularization is thus made more difficult cycle after cycle. The successive growth cycles result in hairs that are finer and finer and shorter and shorter, gradually transforming into an unpigmented down. Certain areas are preferentially affected, especially the temporal or frontal lobes in men, and a diffuse alopecia of the crown of the head in women.

As a result of the fundamental role of the perifollicular capillary circulation mentioned above, any defect in this circulation will result in a reduction in the supply of nutrients and gases (especially oxygen) required for hair growth, leading to disturbances in the growth of the hair and the gradual establishment of alopecia.

The term alopecia also covers a whole family of afflictions of hair follicles whose final consequence is the permanent, partial or general loss of the hair. This is more particularly a matter of androgenic alopecia. In a large number of cases, early loss of hair occurs in genetically predisposed individuals; this is then a matter of androchronogenetic alopecia. This form of alopecia especially affects men.

It is moreover known that certain factors, such as hormonal imbalance, physiological stress or malnutrition, can accentuate the phenomenon of hair loss.

In general, any factor that results in an increase in the blood supply to the hair follicles, either by activating angiogenesis, combating its regression or acting on the capillaries to limit their constriction, will have a beneficial effect on the energy supply required for good growth of these follicles.

Compositions for suppressing or reducing alopecia, and especially for inducing or stimulating hair growth or reducing hair loss have been sought for many years in the cosmetics and pharmaceuticals industries. One of the routes explored is the maintenance of the vascularization around the hair follicle.

Thus, one of the compounds known to maintain perifollicular vascularization is verapamil, which is a powerful type L calcium-channel antagonist ($IC_{50Ca}{}^{2+}$=38 nM). Verapamil and other calcium-channel antagonists such as diltiazem and nifedipine are described as being active in the treatment of hair loss, in particular as a result of their effects on capillary circulation (cf. the documents by Shiseido JP 88/062680 and Coppe J. BE/89/000305). $IC_{50Ca}{}^{2+}$ is the concentration that inhibits 50% of the release of $Ca^{2+}$.

In addition, documents exist describing the use of NO (nitrogen monoxide) donors for application to the scalp, to stimulate hair growth by acting on the capillary circulation of the scalp. Thus, the patent by Proctor (EP-0-327,263) describes the use of compounds producing the NO radical, in combination with reducing agents, antioxidants and hydroxyl-radical scavengers. Another patent by E. Fossel (WO 99/13717) describes the use of arginine and derivatives thereof as an NO-synthase substrate for the in vivo formation of NO and their use (inter alia) in the treatment of alopecia. Another patent by Shiseido (JP-A-07,016,023) also describes the use of arginine and its derivatives in the treatment of alopecia.

These known substances have adverse effects. In particular, they have multiple activities, which may disrupt the ionic and physiological equilibrium of the skin cells. In other words, their multiple activity makes it difficult to control their action on cells.

SUMMARY OF THE INVENTION

The present invention features the use of particular novel compounds for ameliorating or overcoming the above drawbacks. These compounds also exhibit specific local activity. They effect revascularization of the hair follicle, of its peripheral region and/or of the hair after each growth cycle, and also inhibit the formation and establishment of perifollicular fibrosis, a factor which aggravates poor vascularization of the hair.

As a known molecule acting specifically on the formation and establishment of perifollicular fibrosis, mention may be made of aminexil (2,4-diaminopyrimidine N-oxide), described in WO 96/09048, which has inhibitory activity on the expression of lysyl-hydroxylase. Lysyl-hydroxylase and prolyl-hydroxylase are enzymes involved in the formation of collagen fibers, and deregulation of their functioning is one of the factors responsible for the development of perifollicular fibrosis.

GB-A-2-198,132 also discloses the use of 2,6-diaminopyrimidine N-oxide derivatives in compositions for inducing and stimulating hair growth and reducing hair loss.

Thus, after considerable research, novel pyrimidine N-oxide compounds have been developed with specific local activities, on the one hand inhibitory activity on the expression of lysyl-hydroxylase, and, on the other, local, temporary and transient vasodilatory activity furthermore allowing a supply of energy and gases to the hair bulb. In particular, the subject compounds are NO precursors.

The pyrimidine N-oxide derivatives according to the invention thus exert, on contact with the skin and in a sequential manner, a two-fold activity, which allows them to be used advantageously as active agents for stimulating and/or inducing hair growth and/or for reducing hair loss and/or increasing hair density.

It has also been found that the subject compounds have a beneficial effect on the growth of the eyelashes, and also on certain other human hairs. These derivatives also have a beneficial effect on the skin, the lips and the nails.

DETAILED DESCRIPTION OF BEST MODE AND SPECIFIC/PREFERRED EMBODIMENTS OF THE INVENTION

More particularly, the present invention thus features novel pyrimidine N-oxide compounds of formula (A) or salts thereof:

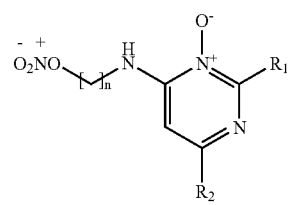

in which n is an integer ranging from 2 to 12; $R_1$ is a linear or branched, saturated or unsaturated alkyl radical, optionally substituted with a group —OR', —NR'R" or —COOR', $R_1$ having from 1 to 20 carbon atoms and preferably from 1 to 10 carbon atoms, or is NR'R"; $R_2$ is hydrogen, —$NR_3R_4$, —$OR_3$, or —$SR_3$, wherein $R_3$ and $R_4$, which may be identical or different, are each a linear or branched, saturated or unsaturated alkyl radical, optionally substituted with a group —OR', —NR'R" or —COOR', $R_2$ having from 1 to 20 carbon atoms and preferably from 1 to 10 carbon atoms, with the proviso that $R_3$ and $R_4$ may form part of a saturated or unsaturated ring member of 4 to 7 atoms, optionally containing at least one hetero atom; and R' and R", which may be identical or different, are each hydrogen or a saturated, linear or branched $C_1$-$C_3$ alkyl radical.

This invention also features compositions containing, in a physiologically acceptable medium, an effective amount of at least one compound of formula (A) or a salt thereof, as defined above. These compositions are useful to induce and/or stimulate the growth of keratin fibers and/or to reduce their loss and/or to increase their density.

The present invention also features administration of at least one compound of formula (A) or a salt thereof, as defined above, as an agent for inducing and/or stimulating the growth of human keratin fibers and/or for reducing their loss and/or for increasing their density. The expression "increasing the density of keratin fibers, and especially, the hair density" means increasing the number of keratin fibers, especially of the hair, per $cm^2$ of skin such as the scalp.

This invention also features the cosmetic use of at least one compound of formula (A) or a salt thereof in a cosmetic care and/or makeup composition for human keratin fibers, to reduce the loss of the keratin fibers and/or to increase their density. The present invention also features the use of at least one compound of formula (A) or a salt thereof for the preparation of a care and/or of a treatment composition for the human keratin fibers, for inducing and/or stimulating the growth of keratin fibers and/or for reducing their loss and/or for increasing their density.

The human keratin fibers to which the invention applies are especially the hair, the eyebrows, the eyelashes, beard hair, moustache hair and pubic hair. More especially, the invention applies to human head hair and/or eyelashes.

In particular, this invention features the cosmetic use of at least one compound of formula (A) or a salt thereof in a human cosmetic haircare composition, as an agent for treating alopecia of natural origin and in particular androgenic or andro-chrono-genetic alopecia, or the use of at least one compound of formula (A) or a salt thereof for the preparation of a human hair composition for treating alopecia of natural origin and in particular androgenic or andro-chrono-genetic alopecia. Thus, this composition makes it possible to keep the hair in good condition and/or to combat the natural loss of the hair, in particular in men.

The present invention also features the cosmetic use of at least one derivative of formula (A) or a salt thereof, as defined above, in a cosmetic care and/or makeup composition for human eyelashes or for the preparation of a care and/or treatment composition for human eyelashes, to induce and/or stimulate the growth of the eyelashes and/or to increase their density. This composition thus makes it possible to keep the eyelashes in good condition and/or to improve their condition and/or appearance.

Too, this invention also features the use of at least one compound of formula (A) or a salt thereof, as an NO-precursor agent. Also featured is the use of at least one compound of formula (A) or a salt thereof for the manufacture of a composition for treating disorders associated with a reduction of the cutaneous capillary circulation or vascularization and especially of a human hair follicle.

And this invention also features the use of at least one compound of formula (A) or a salt thereof as a lysyl-hydroxylase inhibitor, and more specifically as a precursor of a lysyl-hydroxylase inhibitor, and also the use of this compound (A) or a salt thereof for the manufacture of a composition for treating disorders associated with the synthesis and/or release of lysyl-hydroxylase.

As disorders associated with a reduction in capillary circulation and/or in the synthesis and/or release of lysyl-hydroxylase, mention may be made of the deposition of collagen, psoriasis, chronic ulcers, the increase of cellulite and/or fat, and Raynaud's syndrome. Thus, the derivatives of formula (A) may be used for the preparation of an anti-aging or slimming composition or a composition for giving the skin a radiant or luminescent complexion (known as a healthy complexion effect) or for giving colour to the lips, or the preparation of a composition for combating Raynaud's syndrome, ulcers or psoriasis. This composition especially allows a smoothing-out and/or reduction of wrinkles.

Thus, the present invention features the cosmetic use of at least one derivative of formula (A) or a salt thereof, in an anti-aging, anti-wrinkle or slimming cosmetic composition or a cosmetic composition for giving the skin a radiant complexion or a luminescent complexion or for giving colour to the lips, and to the use of at least one compound of formula (A) or a salt thereof, for the preparation of a physiologically acceptable composition for treating the intrinsic and/or extrinsic signs of aging, excess weight, ulcers, Raynaud's syndrome and/or psoriasis and/or for improving skin cicatrization. The signs of extrinsic aging are in particular those caused by ultraviolet radiation (UV lamps or intense sunlight).

By their NO-precursor activity, the derivatives according to the invention also make it possible to combat cutaneous mycosis, inflammatory disorders such as erythema, especially solar erythema or lupus erythema, contact hypersensitivity reactions and/or allergic manifestations, eczema, pruritus, sensitive skin, including sensitive scalp, and also to combat hypermelanosis.

Thus, this invention features the use of at least one compound of formula (A) or a salt thereof, for the manufacture of a physiologically acceptable composition for treating cutaneous mycosis, inflammatory disorders, contact hypersensitivity reactions, allergic manifestations, eczema, pruritus, sensitive skin and/or hypermelanosis.

The present invention also features a cosmetic regime or regimen for treating human keratin fibers and/or the skin, including the scalp, which is especially intended to stimulate the growth of human keratin fibers such as human hair and eyelashes and/or to reduce their loss, comprising topically applying to the human keratin fibers and/or to the skin a cosmetic composition which comprises an effective amount of at least one compound of formula (A) or a salt thereof, leaving this composition in contact with the keratin fibers and/or the skin, and optionally rinsing the keratin fibers and/or the skin.

This treatment has the characteristics of a cosmetic process insofar as it makes it possible to improve the aesthetics of the keratin fibers and in particular of the hair and the eyelashes by giving them greater vigour and an improved appearance. In addition, it may be used daily for several months, without medical prescription.

More especially the present invention features a cosmetic process for caring for human hair and/or the scalp, in order to improve their condition and/or appearance, comprising topically applying to the hair and/or the scalp a cosmetic composition which comprises at least one derivative of formula (A) or a salt thereof, leaving this composition in contact with the hair and/or the scalp, and optionally rinsing the hair and/or the scalp.

Also featured is a cosmetic care and/or makeup process for human eyelashes, in order to improve their condition and/or appearance, comprising topically applying a mascara composition comprising at least one compound of formula (A) or a salt thereof, and leaving this composition in contact with the eyelashes. This mascara composition may be applied alone or as an undercoat for a standard pigmented mascara, and may be removed like a standard pigmented mascara.

This invention also features a process for manufacturing a pyrimidine N-oxide derivative defined above, comprising the following steps:

1) Reaction of compound 5

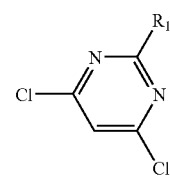

5 with $NH_2(CH_2)_nOH$, n ranging from 2 to 12

2) Oxidation of the product obtained in step 1),

3) Substitution of the product obtained in step 2) to substitute a chlorine atom with a substituent, 4) Nitration of the product obtained in step 3).

In particular, the substitution is a hydrogenation to replace the chlorine atom with a hydrogen atom.

Advantageously, the compounds of formula (A), in salified or un-salified form, show two-fold activity, exerted sequentially on the skin and in particular on the scalp. The compounds A have the particular feature of being inactive in the absence of enzyme and in particular of hydrolases.

In other words, the inactive compounds A release NO in vivo, under the action of skin enzymes (for example hydrolases), which is reflected by a beneficial effect on the capillary circulation: the NO released having a vasodilatory effect.

The compounds A' obtained from inactive A then react as inhibitors "delaying" the expression of enzymes of hydroxylase type and in particular of lysyl-hydroxylase (abbreviated as LH).

The reaction scheme is as follows:

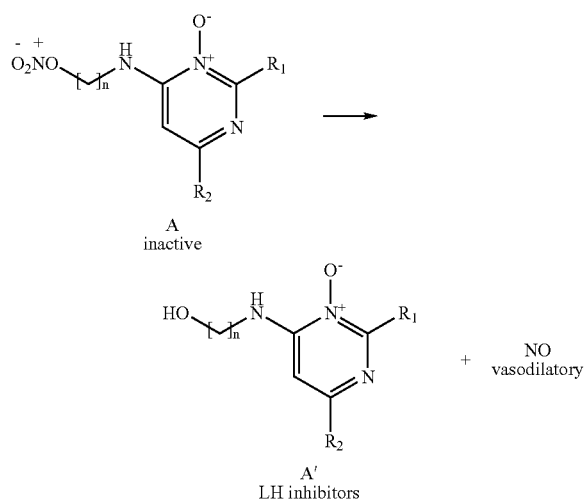

with n, $R_1$ and $R_2$ having the meaning given above.

In the text hereinbelow, and unless specifically mentioned, the use of the term "compound of formula (A)" should be understood as also meaning both the compound of formula (A) in acid or base form, and a salt thereof. It may also be in tautomeric form.

According to the invention, the term "at least one" means one or more (2, 3 or more). In particular the composition may contain one or more compounds of formula (A). This or these compound(s) may be cis or trans isomers or a mixture of cis/trans isomers. They may also be in tautomeric form. This or these compound(s) may be enantiomers and/or diastereoisomers or a mixture of these isomers, in particular a racemic mixture.

According to the invention, $R_3$ and $R_4$ may, separately or together, form part of a ring containing from 4 to 7 atoms and better still 5 or 6 atoms. They may be saturated or unsaturated and may optionally comprise one or more hetero atoms such as S, N or O or combinations thereof and, for example, from 1 to 4 hetero atoms. As saturated carbon-based rings that may be used, mention may be made of the cyclobutyl, cyclopentyl, cyclohexyl or cycloheptyl radical. Heterocycles Hy that may be mentioned include pyridine, piperidine, morpholine, pyrrole, furan, thiophene, imidazole, oxazole, thiazole, pyrazole, pyrimidine, piperazine, pyrazine, pyridazine, triazine, pyrrolidine and thiazolidine rings. Unsaturated carbon-based rings that may be mentioned include the cyclohexenyl or phenyl ring, and aryl radicals that may be mentioned include the phenyl or naphthyl radical. In addition, these rings may optionally be substituted, in particular with a substituent $T_2$ selected from among halogens and linear or branched $C_1$-$C_{10}$ alkyl radicals.

Furthermore, these rings $R_3$ and $R_4$ may be separate or fused to another ring of the same or of different chemical structure.

When $R_3$ and $R_4$ form part of a heterocycle, this heterocycle comprises at least one nitrogen atom as hetero atom and may be, for example, a pyrrolidine, pyrrole, imidazole, triazole, piperidine, morpholine, piperazine, tetrazole, oxazole, isoxazole, pyridazine or pyridine ring. Preferably, $R_3$ and $R_4$ form with the nitrogen atom to which they are attached a heterocycle comprising at least one nitrogen atom as hetero atom.

As examples of alkyl radicals that may be used in the invention, mention may be made of methyl, ethyl, isopropyl, n-butyl, tert-butyl and n-hexyl radicals.

Halogen atoms that may be used include chlorine, fluorine and bromine atoms, and better still fluorine and chlorine atoms.

According to the invention, the compounds of formula (A) are in isolated form, i.e., in non-polymeric form.

Advantageously, at least one radical from among $R_1$ and $R_2$ is a hydrogen atom or a saturated or unsaturated heterocycle Hy.

According to one embodiment of the invention, $R_1$ is NRR', in particular with R and R' representing H.

According to another embodiment of the invention, $R_2$ is $NR_3R_4$, in particular with $R_3$ and $R_4$ forming, with the nitrogen atom to which they are attached, a heterocycle Hy. In particular, this heterocycle is saturated and contains 6 atoms. By way of example, $R_2$ is H and $R_1$ is NRR' with R and R' especially being H; $R_2$ is a saturated heterocycle containing 6 atoms, the hetero atom being nitrogen and $R_1$ is NRR' with R and R' especially being H. The heterocycle is, for example, a piperidine ring.

Preferably, n is an integer ranging from 2 to 8 and better still from 2 to 4.

According to the invention, the expression "salts of the compound of formula (A)" means the organic or mineral salts of a compound of formula (A).

As mineral salts that may be used according to the invention, mention may be made of: sodium or potassium salts, and also zinc ($Zn^{2+}$), calcium ($Ca^{2+}$), copper ($Cu^{2+}$), iron ($Fe^{2+}$), strontium ($Sr^{2+}$), magnesium ($Mg^{2+}$) and manganese ($Mn^{2+}$) salts; hydroxides, carbonates, chlorides, sulphates, citrates, acetates and lactates.

The organic salts that may be used according to the invention are, for example, the salts of triethanolamine, monoethanolamine, diethanolamine, hexadecylamine, N,N,N',N'-tetrakis(2-hydroxypropyl)ethylenediamine and tris (hydroxymethyl)aminomethane.

To the knowledge of the present inventors, no prior art document describes or suggests that the compounds of formula (A) or salts thereof have the property of inducing and/or stimulating the growth of keratin fibers and/or reducing their loss, or that these compounds can be used topically to increase the density of these fibers.

The effective amount of a compound of formula (A) or a salt thereof corresponds to the amount required to obtain the desired result (i.e., in particular to increase the density of keratin fibers or to promote the growth thereof). One skilled in this art is thus capable of evaluating this effective amount, which depends on the nature of the compound used, the person to whom it is applied and the time of this application.

In the text hereinbelow, and unless otherwise mentioned, the amounts of the various ingredients in the composition are given as weight percentages relative to the total weight of the composition.

To give an order of magnitude, according to the invention, the compound of formula (A) or a salt thereof may be used in an amount representing from $10^{-3}$% to 5% of the total weight of the composition and preferably in an amount representing from $10^{-2}$% to 2% of the total weight of the composition, for example from 0.5% to 2%.

The composition of the invention may be for cosmetic or pharmaceutical use. The composition of the invention is preferably for cosmetic use. Thus, the composition must contain a non-toxic, physiologically acceptable medium that can be applied to human skin, including the scalp and the eyelids and to the integuments such as keratin fibers and the lips. For the purposes of the invention, the term "cosmetic" means a composition of pleasant appearance, odour and feel.

The compound of formula (A), salified or not, may be used in a composition that should be ingested, injected or applied to the skin or to keratin fibers (to any area of skin or fibers to be treated).

According to the invention, the compound of formula (A) may be used orally in an amount of from 0.1 to 300 mg per day, for example from 5 to 10 mg/day.

A preferred composition of the invention is a composition for cosmetic use and in particular for topical application to the skin and keratin fibers, and more especially to the scalp, the hair and the eyelashes.

This composition may be in any known presentation form that is suitable for the mode of use.

For topical application to the skin, the composition may be in the form of an aqueous, alcoholic or aqueous-alcoholic solution or suspension, or an oily suspension, an emulsion or dispersion of more or less fluid consistency and especially of liquid or semi-liquid consistency, obtained by dispersion of a fatty phase in an aqueous phase (O/W) or conversely (W/O), a solid (O/W) or (W/O) dispersion or emulsion, a more or less fluid or solid aqueous, aqueous-alcoholic or oily gel, a free or compacted powder to be used in unmodified form or to be incorporated into a physiologically acceptable medium, or alternatively microcapsules, microparticles or vesicular dispersions of ionic and/or nonionic type.

A composition in the form of a foam or alternatively in the form of an aerosol or spray, then comprising a pressurized propellant, is also suitable.

The composition may thus be in the form of a lotion, a serum, a milk, an O/W or W/O cream, an ointment, a pomade, a balm, a patch, an impregnated pad, a soap, a bar or a mousse.

In particular, the composition for application to the scalp or the hair may be in the form of a haircare lotion, for example for daily or twice-weekly application, a shampoo or a hair conditioner, in particular for twice-weekly or weekly application, a liquid or solid scalp-cleansing soap for daily application, a hairstyle shaping product (lacquer, hair setting product or styling gel), a treatment mask, a foaming gel or cream for cleansing the hair. It may also be in the form of a hair dye or mascara to be applied with a brush or a comb.

Moreover, for application to the eyelashes and body hairs, the composition to which the invention applies may be in the form of a pigmented or unpigmented mascara, to be applied with a brush to the eyelashes or alternatively to beard or moustache hair.

For a composition for use by injection, the composition may be in the form of an aqueous lotion or an oily suspension, for example in the form of a serum. For oral use, the composition may be in the form of capsules, granules, drinkable syrups or tablets.

According to one particular embodiment, the composition according to the invention is in the form of a hair cream or hair lotion, a shampoo or conditioner for the hair or a mascara or for the eyelashes.

The amounts of the various constituents of the physiological medium of the composition according to the invention are those generally used in the fields under consideration. In addition, these compositions are prepared according to the usual methods.

When the composition is an emulsion, the proportion of the fatty phase may range from 2% to 80% by weight and preferably from 5% to 50% by weight relative to the total weight of the composition. The aqueous phase is adjusted as a function of the content of fatty phase and of compound(s) (A) and also of that of the optional additional ingredients, to obtain 100% by weight. In practice, the aqueous phase is from 5% to 99.9% by weight.

The fatty phase may contain fatty or oily compounds that are liquid at room temperature (25° C.) and atmospheric pressure (760 mm/Hg), which are generally known as oils. These oils may be mutually compatible or incompatible and may form a macroscopically homogeneous liquid fatty phase or a two-phase or three-phase system.

In addition to the oils, the fatty phase may contain waxes, gums, lipophilic polymers or "pasty" or viscous products containing solid parts and liquid parts.

The aqueous phase contains water and optionally an ingredient that is miscible in all proportions with water, for instance $C_1$ to $C_8$ lower alcohols such as ethanol or isopropanol, polyols, for instance propylene glycol, glycerol or sorbitol, or alternatively acetone or ether.

The emulsifiers and co-emulsifiers used to obtain a composition in emulsion form are those generally used in cosmetics and pharmaceuticals. Their nature also depends on the sense of the emulsion. In practice, the emulsifier and, where appropriate, the co-emulsifier are present in the composition in a proportion ranging from 0.1% to 30% by weight, preferably from 0.5%to 20% by weight and better still from 1% to 8% by weight. The emulsion may also contain lipid vesicles and especially liposomes.

When the composition is in the form of an oily solution or gel, the fatty phase may represent more than 90% of the total weight of the composition.

Advantageously, the composition is an aqueous, alcoholic or aqueous-alcoholic solution or suspension and better still a water/ethanol solution or suspension. The alcoholic fraction may represent from 5% to 99.9% and especially from 8% to 80%.

For a mascara application, the composition is a wax-in-water or wax-in-oil dispersion, a gelled oil or an aqueous gel, which may be pigmented or unpigmented.

The composition of the invention may also comprise other ingredients usually used in the fields under consideration, selected from among solvents, aqueous-phase or oily-phase thickeners or gelling agents, dyes that are soluble in the medium of the composition, solid particles such as fillers or pigments, antioxidants, preservatives, fragrances, electrolytes, neutralizers, UV blockers, for instance sunscreens, film-forming polymers, cosmetic and pharmaceutical active agents with a beneficial effect on the skin or integuments and especially the keratin fibers (such as vitamins) and mixtures thereof. These additives may be present in the composition in the amounts generally used in cosmetics and dermatology, and especially in a proportion of from 0.01% to 50% and better still from 0.1% to 20%, for example from 0.1% to 10%, relative to the total weight of the composition. Depending on their nature, these adjuvants may be introduced into the fatty phase, into the aqueous phase and/or into lipid vesicles and especially liposomes.

Needless to say, one skilled in this art will take care to select the optional additional additives and/or the amount thereof such that the advantageous properties of the composition according to the invention, i.e., in particular the increase in the density of keratin fibers, are not, or are not substantially, adversely affected by the envisaged addition.

As solvents that may be used in the invention, mention may be made of $C_2$ to $C_8$ lower alcohols, for instance ethanol, isopropanol, propylene glycol and certain light cosmetic oils, for instance $C_6$ to $C_{16}$ alkanes.

As oils that may be used in the invention, mention may be made of oils of mineral origin (liquid petroleum jelly or hydrogenated isoparaffin), oils of plant origin (liquid fraction of shea butter, sunflower oil, apricot oil, soybean oil, fatty alcohol or fatty acid), oils of animal origin (perhydrosqualene), synthetic oils (fatty acid esters, purcellin oil), silicone oils (linear or cyclic polydimethylsiloxane, or phenyl trimethicone) and fluoro oils (perfluoropolyethers). Waxes that may be mentioned include silicone waxes, beeswax, candelilla wax, rice wax, carnauba wax, paraffin wax and polyethylene wax.

As emulsifiers that may be used in the invention, examples that may be mentioned include glyceryl stearate, glyceryl laurate, sorbitol stearate, sorbitol oleate, alkyl dimethicone copolyols (with alkyl$\geq$8) and mixtures thereof for a W/O emulsion. Polyethylene glycol monostearate or monolaurate, polyoxyethylenated sorbitol stearate or oleate, and dimethicone copolyols, and mixtures thereof, may also be used for an O/W emulsion.

As hydrophilic gelling agents that may be used in the invention, mention may be made of carboxylvinyl polymers (carbomer), acrylic copolymers such as acrylate/alkylacrylate copolymers, polyacrylamides, polysaccharides such as hydroxypropylcellulose, natural gums and clays, and, as lipophilic gelling agents that may be used in the invention, mention may be made of modified clays, for instance Bentones, metal salts of fatty acids, for instance aluminum stearates, hydrophobic-treated silica and ethylcellulose, and mixtures thereof.

The composition may contain an additional active agent other than the compounds of formula (A), which may be hydrophilic and selected from among proteins, protein hydrolysates, amino acids, polyols, urea, allantoin, sugars and sugar derivatives, water-soluble vitamins, plant extracts (those from Iridacea plants or from soybean) and hydroxy acids (fruit acids or salicylic acid); or lipophilic and selected from among retinol (vitamin A) and its derivatives, especially an ester (retinyl palmitate), tocopherol (vitamin E) and its derivatives (tocopheryl acetate or palmitate), essential fatty acids, ceramides, essential oils, salicylic acid derivatives, for instance 5-n-octanoyl salicylic acid, hydroxy acid esters, and phospholipids, for instance lecithin, and mixtures thereof.

According to one particular embodiment of the invention, the compound of formula (A) or a salt thereof may be combined with at least one additional compound that promotes the regrowth and/or limits the loss of hair. These additional compounds are selected especially from among the lipoxygenase inhibitors as described in EP-0-648,488, the bradykinin inhibitors described especially in EP 0 854 700, prostaglandins and derivatives thereof, especially those described in WO 98/33497, WO 95/11003, JP 97-100 091 and JP 96-134 242, prostaglandin receptor agonists or antagonists, the non-prostanoic prostaglandin analogues as described in EP-1-175,891, EP-1-175,890, WO 01/74307, WO 01/74313, WO 01/74314, WO 01/74315 or WO 01/72268, and mixtures thereof.

As other additional compounds that promote the growth of hair, which may be present in the composition according to the invention, mention may be made of vasodilators, antiandrogens, cyclosporins and analogues thereof, antimicrobial and antifungal agents, anti-inflammatory agents, and retinoids, alone or as a mixture.

The vasodilators that may be used are especially potassium-channel agonists, including Minoxidil, and also the compounds described in U.S. Pat. Nos. 3,382,247, 5,756, 092, 5,772,990, 5,760,043, 5,466,694, 5,438,058 and 4,973, 474, cromakalim, nicorandil and diaxozide, alone or in combination.

The antiandrogens that may be used especially include steroidal and non-steroidal 5$\alpha$-reductase inhibitors, for instance finasteride and the compounds described in U.S. Pat. No. 5,516,779, cyprosterone acetate, azelaic acid and the salts and derivatives thereof, and the compounds described in U.S. Pat. No. 5,480,913, flutamide and the compounds described in U.S. Pat. Nos. 5,411,981, 5,565,467 and 4,910,226.

The antimicrobial or antifungal compounds may be selected from among selenium derivatives, ketoconazole, octopirox, triclocarban, triclosan, zinc pyrithione, itraconazole, asiatic acid, hinokitiol, mipirocine, tetracyclines, especially erythromycin and the compounds described in EP-0-680,745, clinycin hydrochloride, benzoyl peroxide or benzyl peroxide, and minocycline.

The anti-inflammatory agents may be selected from among steroidal anti-inflammatory agents, for instance glucocorticoids, corticosteroids (for example: hydrocortisone) and non-steroidal anti-inflammatory agents, for instance glycyrrhetinic acid and $\alpha$-bisabolol, benzydamine, salicylic acid and the compounds described in EP-0-770,399, WO 94/06434 and FR-2-268,523.

The retinoids may be selected from among isotretinoin, acitretin and tazarotene.

As other additional active compounds for promoting the growth and/or limiting the loss of hair that may be used in combination with the compound of formula (A), which may or may not be salified, mention may be made of aminexil, 6-O-[(9Z,12Z)octadeca-9,12-dienoyl]hexopyranose, benzalkonium chloride, benzethonium chloride, phenol, oestradiol, chlorpheniramine maleate, chlorophylline derivatives, cholesterol, cysteine, methionine, menthol, peppermint oil, calcium pantothenate, panthenol, resorcinol, protein kinase C activators, glycosidase inhibitors, glycosaminoglycanase inhibitors, pyroglutamic acid esters, hexosaccharide or acylhexosaccharide acids, substituted aryl ethylenes, N-acylamino acids, flavonoids, ascomycin derivatives and analogues, histamine antagonists, saponins, proteoglycanase inhibitors, oestrogen agonists and antagonists, pseudoterines, cytokines, growth factor promoters, IL-1 or IL-6 inhibitors, IL-10 promoters, TNF inhibitors, hydroxy acids, benzophenones, hydantoin, retinoic acid; vitamins, for instance vitamin D, vitamin B12 analogues and pantothenol; triterpenes, for instance ursolic acid and the compounds described in U.S. Pat. Nos. 5,529,769, 5,468,888 and 5,631, 282; antipruriginous agents, for instance thenaldine, trimeprazine or cyproheptadine; antiparasitic agents, in particular metronidazole, crotamiton or pyrethroids; antifungal agents, in particular octopirox and compounds belonging to the imidazole family, such as econazole, ketoconazole or miconazole or salts thereof, nicotinic acid esters especially including tocopheryl nicotinate, benzyl nicotinate and $C_1$-$C_6$ alkyl nicotinates, for instance methyl or hexyl nicotinate; calcium antagonists, for instance cinnarizine, diltiazem, nimodipine, verapamil, alverine and nifedipine; hormones such as estriol or its analogues, thyroxine and its salts, or progesterone; antiandrogens such as oxendolone, spironolactone, diethylstilbestrol and flutamide; PF receptor (type-F prostaglandin receptor) agonists such as latonoprost, bimatoprost, travoprost or unoprostone; 15-hydroxyprostaglandine dehydrogenase inhibitors; mixtures thereof.

It is also suitable for the composition comprising at least the compound of formula (A), which may or may not be salified, to be in liposomal form, as described especially in document WO 94/22468. Thus, the compound encapsulated in the liposomes may be delivered selectively to the hair follicle.

The composition according to the invention may be applied to the alopecic areas of the scalp and the hair of an individual, and optionally left in contact for several hours and optionally rinsed out.

The composition containing an effective amount of a compound of formula (A) which may or may not be salified may, for example, be applied in the evening, kept in contact throughout the night and optionally shampooed out in the morning. These applications may be repeated daily for one or more months according to the individual.

Advantageously, in the process according to the invention, between 5 and 500 µl of a solution or composition as defined above, comprising from 0.001% to 5% of the compound of formula (A), is applied to the areas of the scalp to be treated.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

As examples of compounds of formula (A) that may be used in the invention, mention may be made of compounds 1 to 4 below. These compounds give, in the presence of cutaneous enzymes (for example hydrolases) the active compounds 1', 2', 3' and 4', respectively.

Example 1

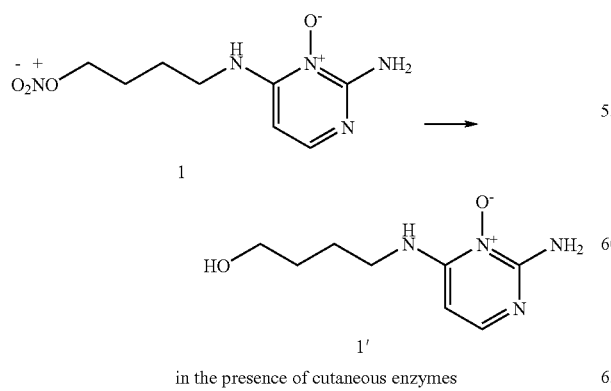

in the presence of cutaneous enzymes

Example 2

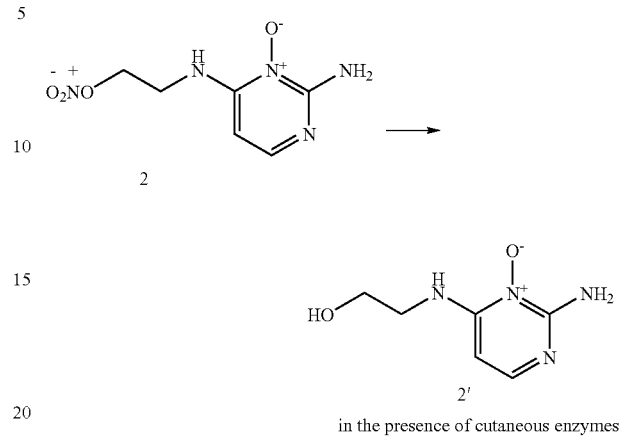

in the presence of cutaneous enzymes

Example 3

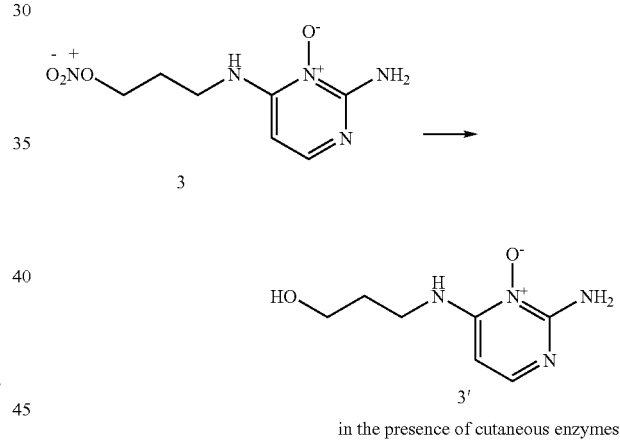

in the presence of cutaneous enzymes

Example 4

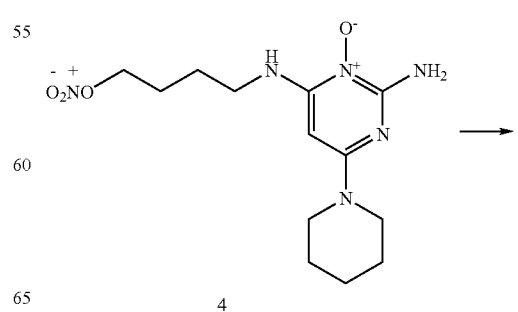

-continued

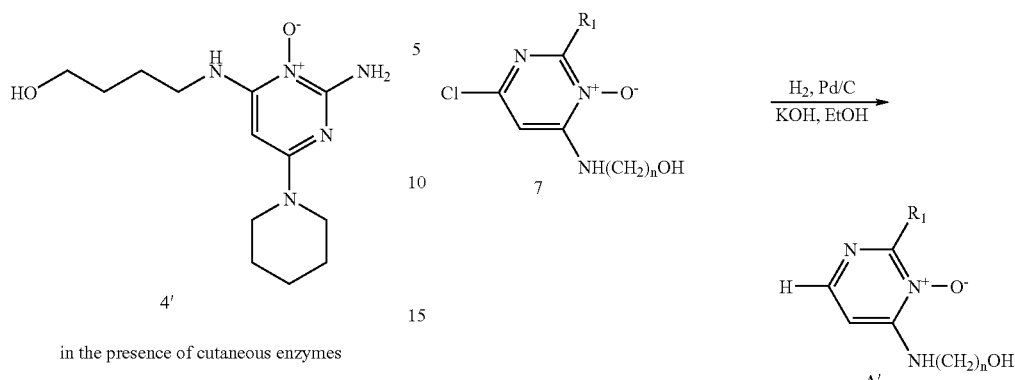

in the presence of cutaneous enzymes

The compounds of formula (A), which may or may not be salified, may be manufactured in a known manner. For example, the synthesis may be performed according to the following reaction scheme:

1st Step:

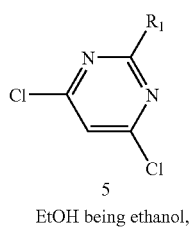

EtOH being ethanol,

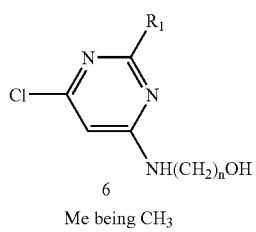

2nd Step:

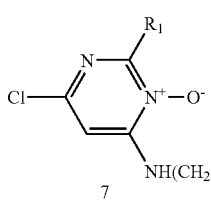

Me being $CH_3$

3rd Step:

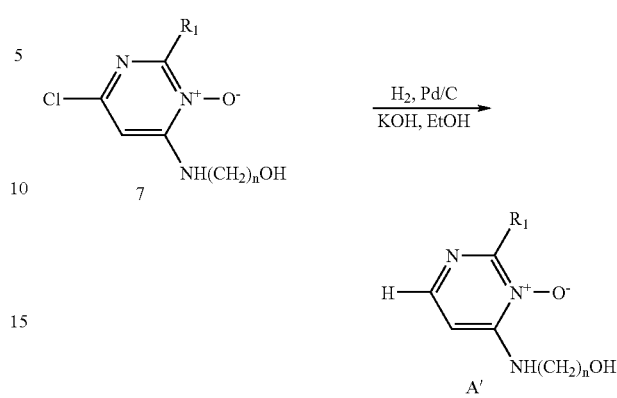

Compound A obtained is then nitrated by the action of fuming $HNO_3$.

Examples of implementation of the invention, which should not in any way limit its scope, will now be given by way of illustration.

Example 1

Synthesis of compound 1':
1st Step:

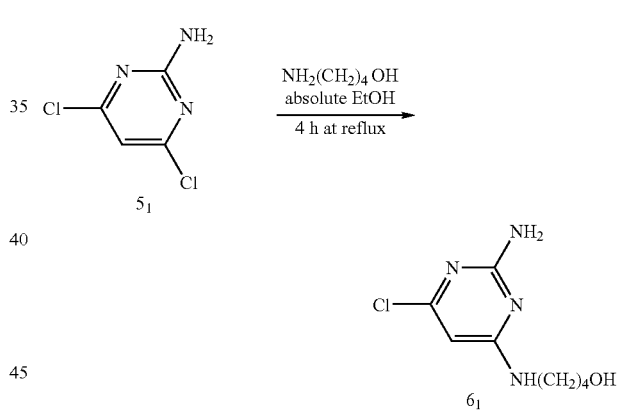

Materials Used:
2-amino-4,6-dichloropyrimidine (compound $5_1$); 21 g (1 eq) [M=164 g/mol],
Butanolamine; 25 g (2.2 eq) [M=89 g/mol],
Absolute EtOH: 150 ml per 10 g.
Procedure:
Introduce the pyrimidine, the absolute ethanol and the butanolamine into a 1-necked flask.
Heat at reflux for 4 hours until everything is dissolved.
Evaporate the medium: a brown oil is obtained. Take up the product in 400 ml of water, stir for 1 hour and filter.
Dry over $P_2O_5$ under vacuum at 50° C.
Monitor by Thin Layer Chromatography (TLC): $CH_2Cl_2$ (9)/MeOH (1), product visible by UV and $I_2$. A more polar spot corresponding to compound 6 is observed. (coefficient of migration: Rf: 0.9)
A beige-coloured product is recovered (M=216.6 g/mol).
Mass recovered: 23 g; yield (Yld): 85%.

Analyses:

Mass spectrum: in accordance (M+H and M−H) with that of compound $6_1$.

Nuclear magnetic resonance (NMR) in DMSO (dimethyl sulphoxide) using a Bruker 400 MHz machine: spectrum in accordance with that of compound $6_1$.

Melting point measured by Dynamic Scanning Colorimetry (DSC): 143-144° C.

2nd Step:

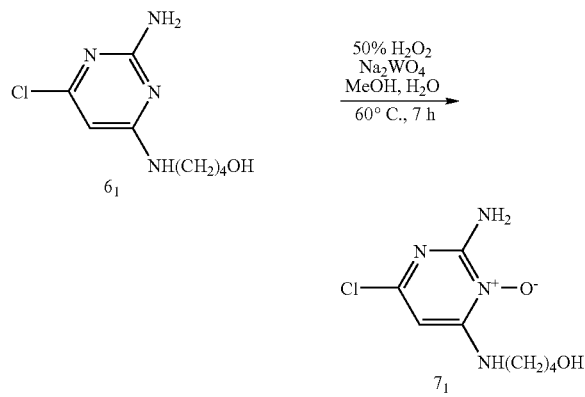

Materials Used:
Compound $6_1$; 23 g, (1 eq) [M: 216.6 g/mol]
50% $H_2O_2$; 14.6 ml (2.4 eq) [M: 34 g/mol/d=1.19]
$Na_2WO_4$: 3.5 g (0.1 eq) [M: 329.86 g/mol]
MeOH: 150 ml
$H_2O$: 3 ml.

Procedure:
Introduce compound $6_1$+MeOH+$H_2O$ in a 3-necked flask and then add $Na_2WO_4$ and 1.2 eq of $H_2O_2$.

Heat for 2 hours at 60° C. Reduce the heating and add a further 1.2 eq of $H_2O_2$.

Continue heating at 60° C. for 5 hours.
Monitor by TLC: 85% $CH_2Cl_2$/15% MeOH/1% $NH_4OH$.
N-oxide developer: 10% $FeCl_3$ solution in EtOH.

Next, allow the reaction medium to cool and add slowly 37.5% sodium hydrogen sulphite solution (100 ml per 20 g) and stir for 1 hour, then check using KI paper that there is no more peroxide.

Next, filter the medium and evaporate. Next, add water and extract 3 times with 100 ml of ethyl acetate. Extract the aqueous phase again (5 times 100 ml) with butanol.

Evaporate off the butanol.
A crystalline solid product of the wax type is recovered.
Mass recovered: 10.6 g; Yld~50%.

Analyses:
TLC: reveals N-oxide (Rf: 0.56),
Mass spectrum in accordance with that of product $7_1$ (ES+=233, ES−=231)

3rd Step:

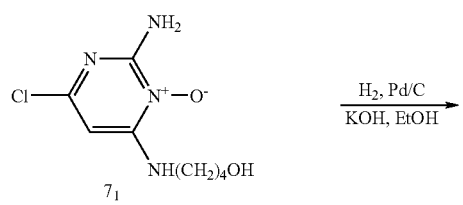

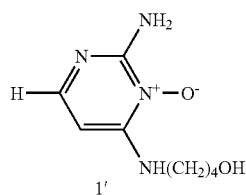

Materials Used:
Compound $7_1$: 10.6 g (1 eq) [M=232.7 g/mol],
KOH: 6.6 g (2.2 eq), [M=56 g/mol],
Absolute EtOH: 600 ml
10% Pd/C, dry: 900 mg.

Procedure:
Mix the potassium hydroxide and the alcohol and then compound $7_1$ until everything is dissolved and filter after 1 hour. Add the Pd/C and hydrogenate with an $H_2$ pressure=10 bar ($10^6$ Pa) at room temperature. Filter through Celite and bring to pH=4-5 with 35% HCl. Filter off the insoluble fraction and evaporate. The product is recovered in ethanol and acetone is then added (30 ml/75 ml). Filter.

The product obtained is off-white.
Mass recovered: 4 g, yield ~45%; [M=198.2 g/mol].

Analyses:
TCL: 80% $CH_2Cl_2$/19% MeOH/1% $NH_4OH$. (Rf: 0.38),
Mass spectrum in accordance with that of compound 1',
400 MHz proton NMR in DMSO: in accordance with that of product 1',
Melting point measured by DSC: 164-165° C.

Biological Results:

NO-Donor Activity of Compound 1 Relative to Compound 1':

The activity of compounds A and A' on inducible NO-synthase was evaluated in the test described by Heck et al. (J. B. C., Vol. 267, No. 30, 21277-21280, 25 Oct. 1992), test of "Modulation of the induction of $NOS_2$ (Inducible Nitric Oxide Synthase) on normal human keratinocytes". The aim of this test is to evaluate the final nitrate and nitrite concentration, after stimulation of NO-synthase 2 or application of an NO donor; it is performed by comparison with the stimulation of cytokine-inducible NO-synthase. The final nitrate and nitrite concentration corresponds to the concentration of NO released.

The test is performed on a culture of normal human keratinocytes obtained from samples. The induction of inducible NO-synthase ($NOS_2$) was brought about by the addition of a combination of several cytokines to the culture medium. The test products were applied at three concentrations ranging from 10 to 1000 μM.

The following controls were introduced into the test:
A: Positive control (induction of the enzyme on stimulated cells): mixtures of interferon-γ (1000 μ/ml) and of interleukin 1-β (100 μ/ml) corresponding to 100% inhibition;
B: Basal control of the unstimulated cells (without cytokines), corresponding to 0% inhibition.

To determine the activity of the test products, the amount of stable NO reaction products (nitrites and nitrates) is measured using the "Nitric Colorimetric Assay" kit sold by the company Boehringer under the reference 1756.28.

The compounds were tested at concentrations of 100 μM, 500 μM and 1000 μM in ethanol.

| Test product | Concentration | % inhibition |
|---|---|---|
| A |  | 100 |
| B |  | 0 |
| 1 | 100 μM | 0 |
| 1 | 500 μM | 18.23% |
| 1 | 1000 μM | 192.47% |
| 1' | 500 μm | NE* |
| 1' | 1000 μm | NE* |
| 2 | 100 μM | 38.77 |
| 2 | 500 μM | 292.57 |
| 2 | 1000 μm | 355.2 |
| 2' | 500 μm | NE |
| 2' | 1000 μm | NE |
| 3 | 100 μM | 34043 |
| 3 | 500 μm | 296.17 |
| 3 | 1000 μm | 361.17 |
| 3' | 500 μm | NE* |
| 3' | 1000 μm | NE* |

*NE means: no effect

From the above table, it is concluded that compounds 1, 2 and 3 have an NO-donating effect, unlike products 1', 2' and 3'.

Activity on Inhibiting the Expression of LH:

a) Test:

Normal human dermal fibroblasts (NHDF) are precultured at high density for 48 hours in MEM199 medium (Gibco) supplemented with 1% foetal calf serum and then treated or not treated with compound 1' or 1 for 6 hours. The cell carpets are then washed with phosphate-buffered saline (PBS) and then frozen in Tri-reagent medium (Sigma). The total RNAs obtained are extracted with Tri-reagent (Sigma) according to the supplier's protocol. A further extraction is performed using chloroform and the RNAs are then precipitated from isopropanol. After removal of the contaminating traces of DNA by treatment with the DNA-free system (Ambion), a reverse transcription of the RNAs into complementary DNA is performed in the presence of oligo dT and the enzyme superscript II (Gibco).

A pair of primers allowing the amplification of specific LH fragments (516 bp; Mahéet al., 1996, Skin Pharmacol. 9, 177-183) and of specific primers of the sequence of collagen I (420 pb) and β-Actin (500 bp, internal reaction standard) were used for the polymerization chain reaction (PCR) with the PCR Supermix system (Gibco) under the following conditions: 94° C. for 2 minutes and then 25 times (95° C.-1 min, 55° C.-1 min, 72° C.-2 min), the chain reaction being terminated by an elongation cycle of 7 minutes at 72° C.

The amplified fragments are then analysed by electrophoresis on agarose gel (1.5%) in the presence of ethidium bromide. The images were captured on GelPrint 2000i (Biophotonics Corp); the densitometric analyses were obtained using the One D-Scan software (Scanalytics).

The results are expressed as a percentage of expression of LH over the β-Actin internal standard (LH/actine) or relative to the collagen messenger RNA (LH/collagen). A reduction of one or of the two percentages indicates a transcriptional inhibition of the relative expression of lysyl hydroxylase and, by analogy, with the molecule 2-4 DPO, (Mahéet al. 1996, Skin Pharmacol. 9. 177-183) a possible use for limiting the abnormal crosslinking of collagen in alopecia.

|  | LH/actine ratio | LH/collagen ratio |
|---|---|---|
| Control | 100 | 100 |
| Compound 1 | 123 | 133 |
| Compound 1' | 64 | 76 | b) Results:

Derivative 1 shows no inhibitory activity on the expression of lysyl-hydroxylase messenger RNA. On the other hand, compound 1' at 10 μM has this capacity of inhibiting by −24% to −36% the expression of lysyl-hydroxylase by human fibroblasts in culture.

Example 2

Synthesis of Compound 2':
1st Step:

<chemical structure: 2-amino-4,6-dichloropyrimidine ($5_2$) reacting with $NH_2CH_2CH_2OH$ in absolute EtOH, 4 h at reflux, yielding compound $6_2$ with NH$_2$, Cl, and NHCH$_2$CH$_2$OH substituents>

Materials Used:
2-amino-4,6-dichloropyrimidine (compound $5_2$): 20 g, (1 eq) [M=164 g/mol],
Ethanolamine: 16.3 g, (2.2 eq) [M=61 g/mol/d=1.016],
Absolute EtOH: 300 ml.

Procedure:

Introduce compound $5_2$, the absolute ethanol and the ethanolamine into a 1-necked flask.

Heat at reflux for 4 hours until everything has dissolved. Evaporate the medium; a brown oil is obtained, which is dissolved in 200 ml of acetic acid and 300 ml of water are then added. Next, extract 6 times with acetic acid. Dry the organic phases over anhydrous Na$_2$SO$_4$ and then evaporate.

Take up the product in isopropyl ether, stir for 1 hour and filter. Dry under vacuum at 50° C.

Monitoring by TLC: CH$_2$Cl$_2$ (9)/MeOH (1), product visible by UV and I$_2$; the more polar spot corresponds to compound $6_2$; Rf: 0.24.

Mass recovered: 17 g; Yld 75%.

Beige-coloured product [M=188.6 g/mol].

Analyses:

Mass spectrum: in accordance (M+H and M−H) with that of compound $6_2$.

400 MHz NMR spectrum in DMSO: in accordance with that of product $6_2$.

Melting point measured by DSC: 150-151° C.

2nd Step

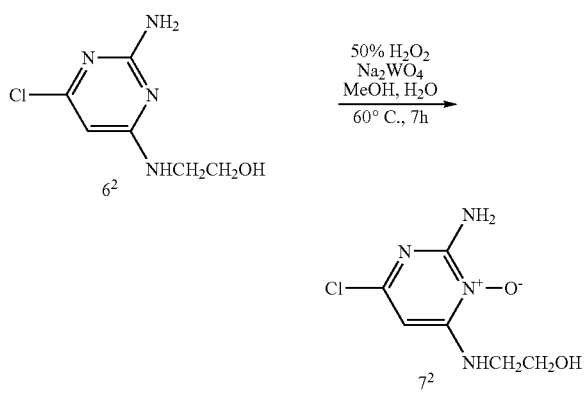

Materials Used:
Compound 6₂: 17 g (1 eq) [M: 188.6 g/mol],
50% H$_2$O$_2$: 12.4 ml (2.4 eq), [M: 34 g/mol/d=1.19],
Na$_2$WO$_4$: 3 g (0.1 eq) [M: 329.86 g/mol],
MeOH: 100 ml,
H$_2$O: 3 ml.
Procedure:
Introduce compound 6₂+MeOH+H$_2$O into a 3-necked flask, add Na$_2$WO$_4$ and 1.2 eq of H$_2$O$_2$.

Heat at 60° C. for 2 hours. Reduce the heating and add a further 1.2 eq of H$_2$O$_2$.

Continue heating at 60° C. for 5 hours.

Monitoring by TLC: CH$_2$Cl$_2$ 85% /MeOH 15% /NH$_4$OH 1%.

N-oxide developer: 10% FeCl$_3$ solution in EtOH, (brown spot), Rf: 0.33.

Next, allow the reaction medium to cool and slowly add 37.5% sodium hydrogen sulphite solution (100 ml per 20 g) and stir for 1 hour, then check using KI paper that there is no more peroxide. Filter off the insoluble fractions from the reaction medium and then evaporate. Next, add water and extract 3 times with 100 ml of ethyl acetate. Extract the aqueous phase again (5 times 100 ml) with butanol. Evaporate off the butanol. A paste is recovered.

Mass recovered: 10.5 g, Yld ~50%.

Analyses:
TLC: reveals N-oxide

3rd Step:

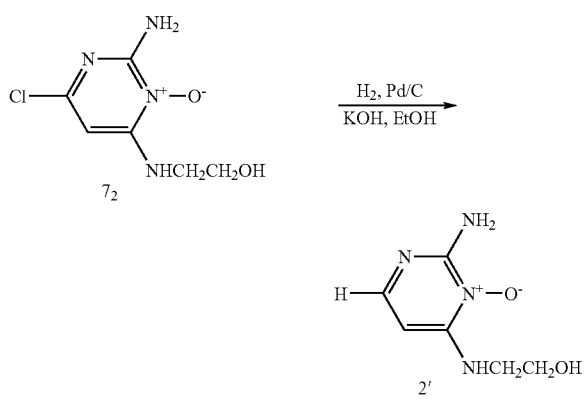

Materials Used:
Compound 7₂: 10.5 g (1 eq), [M=204.6 g/mol],
KOH: 8 g (2.2 eq), [M=56 g/mol],
Absolute EtOH: 600 ml,
10% dry Pd/C: 1.2 g.
Procedure
Mix the potassium hydroxide and the alcohol and then compound 7₂ until everything has dissolved, and filter after 1 hour. Add the Pd/C and hydrogenate with an H$_2$ pressure=10 bar (10$^6$ Pa) at room temperature. Filter through Celite and bring to pH=4-5 with 35% HCl. Filter off the insoluble fractions and evaporate. The product is recovered in ethanol, which is heated and acetonitrile is then added (15 ml/100 ml). Allow the mixture to cool to room temperature and then filter.

An off-white product is obtained.
Mass recovered: 2.4 g, Yield ~30%; M=170.2 g/mol.
Analyses:
TLC: 80% CH$_2$Cl$_2$/19% MeOH/1% NH$_4$OH, (Rf: 0.3)
Mass spectrum in accordance with that of Compound 2'.
400 MHz proton NMR spectrum in DMSO: in accordance with that of product 2'.
Melting point: 186-187° C.

Examples 3 and 4

Synthesis of Compound 3':
Compound 3' was prepared via the same synthetic route and the same procedures as those of compounds 1' and 2'.

Synthesis of Compound 4':

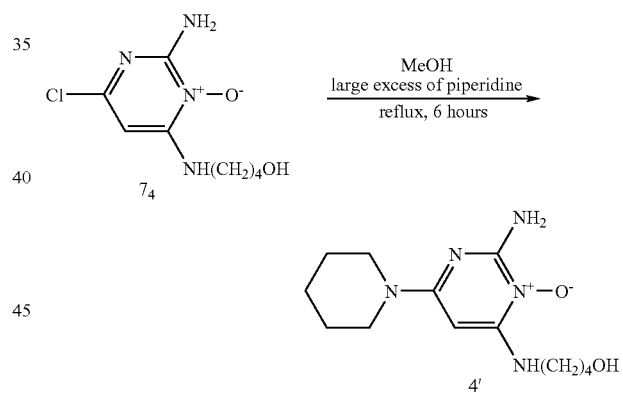

Compound 7₄: 1.5 g, (M=232.6 g/mol),
Piperidine: 5 ml, (M=8.15 g/mol)
MeOH: 30 ml.
Procedure:
Introduce compound 7₄ with 30 ml of MeOH into a reactor, add 2 ml of piperidine and bring to reflux. After heating for 3 hours, add a further 3 ml of piperidine and reflux for a further 3 hours. There is no more starting product on the plate. Monitoring by TLC: CH$_2$Cl$_2$ 85%/MeOH 15%/NH$_4$OH 1%.

Concentrate the reaction medium and then take up the residue with water. Wash with dichloromethane and extract 3 times with butanol. Evaporate off the butanol. A semi-solid, semi-liquid residue is obtained. Take up this residue in 10 ml of acetonitrile with stirring. A solid disperses finely. After stirring overnight, filter and rinse twice with 15 ml of acetone. Dry in a desiccator under vacuum.

Mass recovered: 0.250 g; Yld 14% (M=281.35 g/mol).
Analyses:
200 MHz proton NMR spectrum in DMSO: in accordance with that of compound 4'.
General Method for Nitrating the Molecules:

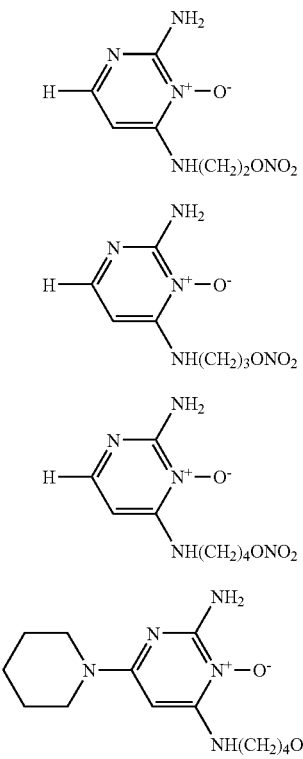

Materials Used:
Starting product: 1 g,
Fuming HNO$_3$: 5 ml.
Procedure:
Introduce fuming HNO$_3$ into a round-necked flask and cool to 0° C. Add the starting product portionwise. Stir for 1 hour at 0° C. Monitoring by TLC:
80% CH$_2$Cl$_2$/19% MeOH/1% NH$_4$OH. Pour the reaction medium into a water/ice mixture (≈30 ml). Bring the pH to 9 with 35% NaOH solution. Extract with butanol, evaporate and take up the residue in 5 ml of acetone. Dry in a desiccator under vacuum at room temperature.
Analyses:
400 MHz proton NMR spectrum in DMSO, in accordance with those of compounds 1 to 4.

The compositions below are obtained by the usual techniques commonly used in cosmetics or pharmaceutics.

Example 5

Hair Lotion

| | |
|---|---|
| Compound 1 | 1.00 g |
| Propylene glycol | 30.00 g |
| Ethyl alcohol | 40.00 g |
| Water | qs 100.00 g |

This lotion is applied to the scalp once or twice a day, at a rate of 1 ml per application, massaging the scalp gently to help the active agent to penetrate. The hair is then dried in the open air. This lotion makes it possible to reduce hair loss and to promote regrowth of the hair.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pyrimidine N-oxide compound having the formula (A)

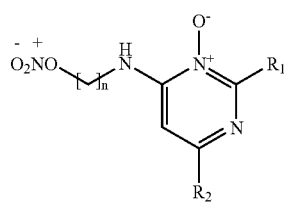

in which n is an integer ranging from 2 to 12; $R_1$ is a linear or branched, saturated or unsaturated alkyl radical, optionally substituted with a group —OR', —NR'R" or —COOR', $R_1$ having a total of from 1 to 20 carbon atoms, or $R_1$ is NR'R"; $R_2$ is hydrogen, —NR$_3$R$_4$, —OR$_3$, or —SR$_3$, wherein $R_3$ and $R_4$, which may be identical or different, are each a linear or branched, saturated or unsaturated alkyl radical, optionally substituted with a group —OR', —NR'R" or —COOR', $R_2$ when not hydrogen having a total of from 1 to 20 carbon atoms, with the proviso that $R_3$ and $R_4$ may form part of a saturated or unsaturated ring member of 4 to 7 atoms, optionally containing at least one hetero atom; and R' and R", which may be identical or different, are each hydrogen or a saturated, linear or branched $C_1$-$C_3$ alkyl radical, or salt thereof.

2. The pyrimidine N-oxide compound as defined by claim 1, wherein formula (A), $R_1$ and $R_2$ each have a total of from 1 to 10 carbon atoms.

3. The pyrimidine N-oxide compound as defined by claim 1, wherein formula (A), n ranges from 2 to 6.

4. The pyrimidine N-oxide compound as defined by claim 1, wherein formula (A), n ranges from 2 to 4.

5. The pyrimidine N-oxide compound as defined by claim 1, wherein formula (A), $R_2$ is hydrogen.

6. The pyrimidine N-oxide compound as defined by claim 1, wherein formula (A), $R_1$ is —NR'R".

7. The pyrimidine N-oxide compound as defined by claim 6, wherein formula (A), R' and R" are each hydrogen.

8. The pyrimidine N-oxide compound as defined by claim 1, wherein formula (A), $R_2$ is —NR$_3$R$_4$.

9. The pyrimidine N-oxide compound as defined by claim 8, wherein formula (A), $R_3$ and $R_4$ together form a part of a heterocyclic ring member.

10. The pyrimidine N-oxide compound as defined by claim 8, wherein formula (A), $R_3$ and $R_4$ together form a heterocyclic ring member with the nitrogen atom from which they depend.

11. The pyrimidine N-oxide compound as defined by claim 1, wherein formula (A), $R_2$ is hydrogen and $R_1$ is —NR'R", in which R' and R" are each hydrogen.

12. The pyrimidine N-oxide compound as defined by claim 1, wherein formula (A), $R_2$ is a saturated nitrogenous hetercycle having 6 atoms and $R_1$ is —NR'R", in which R' and R" are each hydrogen.

13. A salt of the pyrimidine N-oxide compound as defined by claim 1, selected from the group consisting of the sodium and potassium salts, the zinc ($Zn^{2+}$), calcium ($Ca^{2+}$), copper ($Cu^{2+}$), iron ($Fe^{2+}$), strontium ($Sr^{2+}$), magnesium ($Mg^{2+}$) and manganese ($Mn^{2+}$) salts, the triethanolamine, monoethanolamine, diethanolamine, hexadecylamine, N,N,N',N'-tetrakis(2-hydroxypropyl)-ethylenediamine and tris(hydroxymethyl)aminomethane salts, and the hydroxides, carbonates, chlorides, sulphates, citrates, acetates and lactates.

14. The pyrimidine N-oxide compound as defined by claim 1, having one of the following formulae:

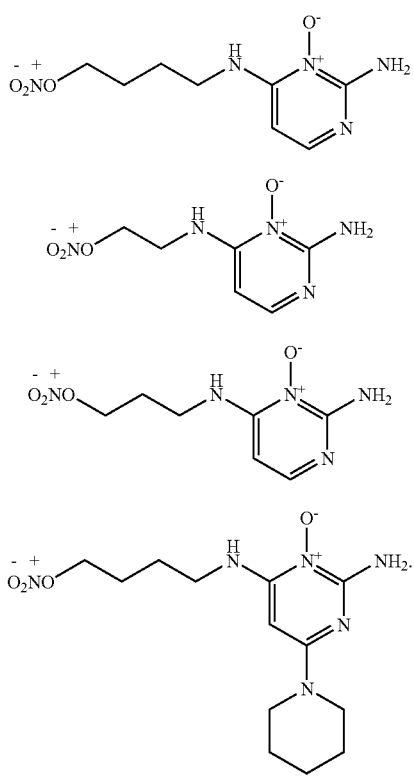

15. A process for the preparation of a pyrimidine N-oxide compound as defined by claim 1 comprising the following steps 1) reacting compound 5

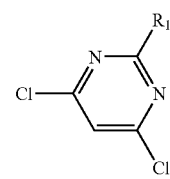

with $NH_2(CH_2)_nOH$, n ranging from 2 to 12, 2) oxidizing the product obtained in step 1), 3) hydrogenating the product obtained in step 2) to replace the chlorine atom with a hydrogen atom, and 4) nitrating the product obtained in step 3).

16. A composition comprising a pyrimidine N-oxide compound as defined by claim 1, or salt thereof, formulated into a physiologically acceptable medium therefor.

17. A composition comprising a pyrimidine N-oxide compound as defined by claim 1, or salt thereof, formulated into a topically applicable, physiologically acceptable medium therefor.

18. The composition as defined by claim 17, comprising a hair cream, a hair lotion, a shampoo, a hair conditioner or a mascara.

19. The composition as defined by claim 17, comprising an aqueous, alcoholic, or aqueous/alcoholic solution or suspension.

20. The composition as defined by claim 16, further comprising at least one other ingredient selected from the group consisting of solvents, aqueous-phase and oily-phase thickeners and gelling agents, dyes that are soluble in the medium of the composition, fillers, pigments, antioxidants, preservatives, fragrances, electrolytes, neutralizers, film-forming polymers, UV blockers, vitamins and mixtures thereof.

21. A method for inhibiting the expression of the enzyme lysyl-hydroxylase in dermal fibroblast cells, or donating NO to keratinocyte cells, comprising administering to said cells a thus effective amount of the pyrimidine N-oxide compound as defined by claim 1, or salt thereof.

\* \* \* \* \*

UNITED STATES PATENT AND TRADEMARK OFFICE
CERTIFICATE OF CORRECTION

| | | |
|---|---|---|
| PATENT NO. | : 7,326,717 B2 | Page 1 of 1 |
| APPLICATION NO. | : 10/839176 | |
| DATED | : February 5, 2008 | |
| INVENTOR(S) | : Maria Dalko et al. | |

It is certified that error appears in the above-identified patent and that said Letters Patent is hereby corrected as shown below:

On Title Page item (30) Foreign Application Priority Data: change "1930" to --2003--.

Signed and Sealed this

Third Day of June, 2008

JON W. DUDAS
*Director of the United States Patent and Trademark Office*